United States Patent
Ang et al.

(10) Patent No.: US 9,538,934 B2
(45) Date of Patent: Jan. 10, 2017

(54) BRAIN-COMPUTER INTERFACE SYSTEM AND METHOD

(75) Inventors: Kai Keng Ang, Singapore (SG); Cuntai Guan, Singapore (SG); Zheng Yang Chin, Singapore (SG); Haihong Zhang, Singapore (SG); Kok Soon Phua, Singapore (SG); Chuan Chu Wang, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 1028 days.

(21) Appl. No.: 13/638,355

(22) PCT Filed: Mar. 31, 2010

(86) PCT No.: PCT/SG2010/000127
§ 371 (c)(1),
(2), (4) Date: Jan. 29, 2013

(87) PCT Pub. No.: WO2011/123059
PCT Pub. Date: Oct. 6, 2011

(65) Prior Publication Data
US 2013/0138011 A1 May 30, 2013

(51) Int. Cl.
*A61B 5/00* (2006.01)
*A61B 5/04* (2006.01)
(Continued)

(52) U.S. Cl.
CPC ............. *A61B 5/0482* (2013.01); *A61B 5/048* (2013.01); *A61B 5/04014* (2013.01);
(Continued)

(58) Field of Classification Search
CPC . A61B 5/04014; A61B 5/04017; A61B 5/048; A61B 5/742; A61B 5/7285; A61B 5/0482; G06F 3/015; G06F 3/016
See application file for complete search history.

(56) References Cited

U.S. PATENT DOCUMENTS

| | | | |
|---|---|---|---|
| 2004/0267152 A1 | 12/2004 | Pineda | |
| 2007/0179534 A1* | 8/2007 | Firlik | A61M 5/14276 607/3 |
| 2009/0099627 A1* | 4/2009 | Molnar | A61B 5/04014 607/62 |

FOREIGN PATENT DOCUMENTS

| | | | |
|---|---|---|---|
| WO | WO 03/037231 A1 | 5/2003 | |
| WO | WO 2008/097201 A1 | 8/2008 | |

OTHER PUBLICATIONS

Kai Keng Ang et al. "Filter Bank Common Spatial Pattern (FBCSP)in Brain-Computer Interface" IEEE World Congress on Computational Intelligence & International Joint Conference on Neural Networks (IJCNN), pp. 2390-2397, DOI: 10.1109/IJCNN.2008.4634130, Hong Kong, Jun. 1-8, 2008.*

(Continued)

*Primary Examiner* — Christine H Matthews
*Assistant Examiner* — Joshua D Lannu
(74) *Attorney, Agent, or Firm* — Choate, Hall & Stewart LLP; Charles E. Lyon

(57) ABSTRACT

A method of training a classification algorithm for a Brain Computer Interface (BCI). The method includes the steps of: dividing a Electroencephalography (EEG) signal into a plurality of time segments; for each time segment, dividing a corresponding EEG signal portion into a plurality of frequency bands; for each frequency band, computing a spatial filtering projection matrix based on a Common Spatial Pattern (CSP) algorithm and a corresponding feature, and computing mutual information of each corresponding feature with respect to one or more motor imagery classes; for each time segment, summing the mutual information of (Continued)

all the corresponding features with respect to the respective classes; and selecting the corresponding features of the time segment with a maximum sum of mutual information for one class for training classifiers of the classification algorithm.

14 Claims, 12 Drawing Sheets

(51) Int. Cl.
    *A61B 5/0482*     (2006.01)
    *A61B 5/048*     (2006.01)
    *G06F 3/01*     (2006.01)

(52) U.S. Cl.
    CPC .......... *A61B 5/04017* (2013.01); *A61B 5/742* (2013.01); *G06F 3/015* (2013.01); *G06F 3/016* (2013.01); *A61B 5/7285* (2013.01)

(56) References Cited

OTHER PUBLICATIONS

Ang et al., Filter Bank Common Spatial Pattern (FBCSP) in Brain-Computer Interface, IEEE World Congress on Computational Intelligence & International Joint Conference on Neural Networks (IJCNN), 2390-2397 (2008).

Arvaneh et al., Optimizing EEG Channel Selection by Regularized Spatial Filtering and Multi Band Signal Decomposition, Proceedings of the 7th IASTED Intl. Conf. Biomedical Engineering, 86-90 (2010).

Hamadicharef et al., Learning EEG-based Spectral-Spatial Patterns for Attention Level Measurement, IEEE International Symposium on Circuits and Systems (ISCAS), 1465-1468 (2009).

Zhang et al., An Algorithm for Idle-State Detection in Motor-Imagery-Based Brain-Computer Interface, Computational Intelligence and Neuroscience, 39714, 1-9 (2007).

International Search Report for PCT/SG10/00127, 2 pages (issued Jan. 17, 2011).

Written Opinion for PCT/SG10/00127, 5 pages (issued Jan. 17, 2011).

International Search Report for PCT/SG11/00137, 5 pages (issued Aug. 20, 2011).

Written Opinion for PCT/SG11/00137, 7 pages (issued Aug. 20, 2011).

Singapore Written Opinion of 201207226-0, 5 pages (issued Aug. 29, 2013).

\* cited by examiner

BRAIN-COMPUTER INTERFACE SYSTEM AND METHOD

FIELD OF INVENTION

The invention relates to a non-invasive EEG-based brain-computer interface.

BACKGROUND

Brain computer interfaces (BCIs) function as a direct communication pathway between a human brain and an external device. Furthermore, BCI systems can also provide an important test-bed for the development of mathematical methods and multi-channel signal processing to derive command signals from brain activities. As it directly uses the electrical signatures of the brain's activity for responding to external stimuli, it is particularly useful for paralyzed people who suffer from severe neuromuscular disorders and are hence unable to communicate through the normal neuromuscular, pathway. The electroencephalogram (EEG) is one of the widely used techniques out of many existing brain signal measuring techniques due to its advantages such as its non-invasive nature and its low cost.

In addition to rehabilitation, BCI applications include, but are not limited to, communication, control, biofeedback and interactive computer gaming and entertainment computing.

For example, currently, stroke rehabilitation commonly involves physical therapy by human therapists. Alternatively, robotic rehabilitation may augment human therapists and enable novel rehabilitation exercises which may not be available from human therapists.

Typically, robotic rehabilitation includes rehabilitation based solely on movement repetition. In other words, a robot assists the patient even if the patient is not attentive towards therapy and robot assistance is triggered if no movement detected, for example, after a period of 2 seconds.

Moreover, robots deliver standardized rehabilitation, unlike human therapists who can deliver individualized rehabilitation based on the condition and progress of the stroke patient. Furthermore, the use of a robot may not be suitable for home-based rehabilitation where there are cost and space concerns. In addition, the main form of feedback to the patient is visual feedback provided through a screen, which may be insufficient.

Clinical trials involving brain-computer interface (BCI) based robotic rehabilitation are currently ongoing and some advantages over standard robotic rehabilitation include robotic assistance to the patient only if motor intent is detected and detection of motor intent being calibrated to patient-specific motor imagery electroencephalogram (EEG).

Embodiments of the present invention seek to improve on current brain-computer interface systems.

SUMMARY

According to a first aspect of the present invention, there is provided a method for brain-computer interface (BCI) based interaction, the method comprising the steps of: acquiring a person's EEG signal; processing the EEG signal to determine a motor imagery of the person; detecting a movement of the person using a detection device; and providing feedback to the person based on the motor imagery, the movement, or both; wherein providing the feedback comprises activating a stimulation element of the detection device for providing a stimulus to the person.

The method may comprise processing the EEG signal to determine whether a specific motor imagery is performed by the person and activating the stimulation element if the specific motor imagery is performed.

The feedback may further comprise a separate visual feedback to the person if the specific motor imagery is performed.

The method may comprise determining whether a specific movement is performed by the person and activating the stimulation element if the specific movement is performed.

The feedback may further comprise a separate visual feedback to the person if the specific movement is performed.

The determining whether the specific movement is performed by the person may occur over a period of time.

The processing of the EEG signal may comprise using a trained classification algorithm.

Training the classification algorithm may comprise: dividing the EEG signal into a plurality of segments, for each segment, dividing a corresponding EEG signal portion into a plurality of frequency bands, for each frequency band, computing a spatial filtering projection matrix based on a CSP algorithm and a corresponding feature, and computing mutual information of each corresponding feature with respect to one or more motor imagery classes; for each segment, summing the mutual information of all the corresponding with respect to the respective classes, and selecting the corresponding features of the segment with a maximum sum of mutual information for one class for training.

The method may further comprise training classifiers of the classification algorithm using the selected corresponding features.

Training the classifiers may comprise non-linear regression using the selected corresponding features and non-linear post-processing regression using an output from the non linear regression.

Computing the spatial filtering projection matrix based on the CSP algorithm may comprise using a multi-modal multi-time segment for each frequency band.

The multi-modal multi-time segment for each frequency band may comprise a multi-modal representation of an idle state.

According to a second aspect of the present invention, there is provided a brain-computer interface system comprising: means for acquiring a person's EEG signal; means for processing the EEG signal to determine a motor imagery of the person; means for detecting a movement of the person using a detection device; and means for providing feedback to the person based on the motor imagery, the movement, or both; wherein the means for providing the feedback comprises a stimulation element of the detection device for providing a stimulus to the person.

The stimulation element may comprise a tactile actuator.

The system may further comprise a screen for providing visual feedback to the person based on the motor imagery, the movement, or both.

According to a third aspect of the present invention, there is provided a method of training a classification algorithm for a BCI, the method comprising the steps of: dividing a EEG signal into a plurality of segments, for each segment, dividing a corresponding EEG signal portion into a plurality of frequency bands, for each frequency band, computing a spatial filtering projection matrix based on a CSP algorithm and a corresponding feature, and computing mutual information of each corresponding feature with respect to one or more motor imagery classes; for each segment, summing the mutual information of all the corresponding features with respect to the respective classes, and selecting the corresponding features of the segment with a maximum sum of mutual information for one class for training classifiers of the classification algorithm.

Training the classifiers may comprise non-linear regression using the selected corresponding features and non-linear post-processing regression using an output from the non linear regression.

Computing the spatial filtering projection matrix based on the CSP algorithm may comprise using a multi-modal multi-time segment for each frequency band.

The multi-modal multi-time segment for each frequency band may comprise a multi-modal representation of an idle state.

BRIEF DESCRIPTION OF THE DRAWINGS

Example embodiments of the invention will be better understood and readily apparent to one of ordinary skill in the art from the following written description, by way of example only, and in conjunction with the drawings, in which.

DETAILED DESCRIPTION

Figure 1:
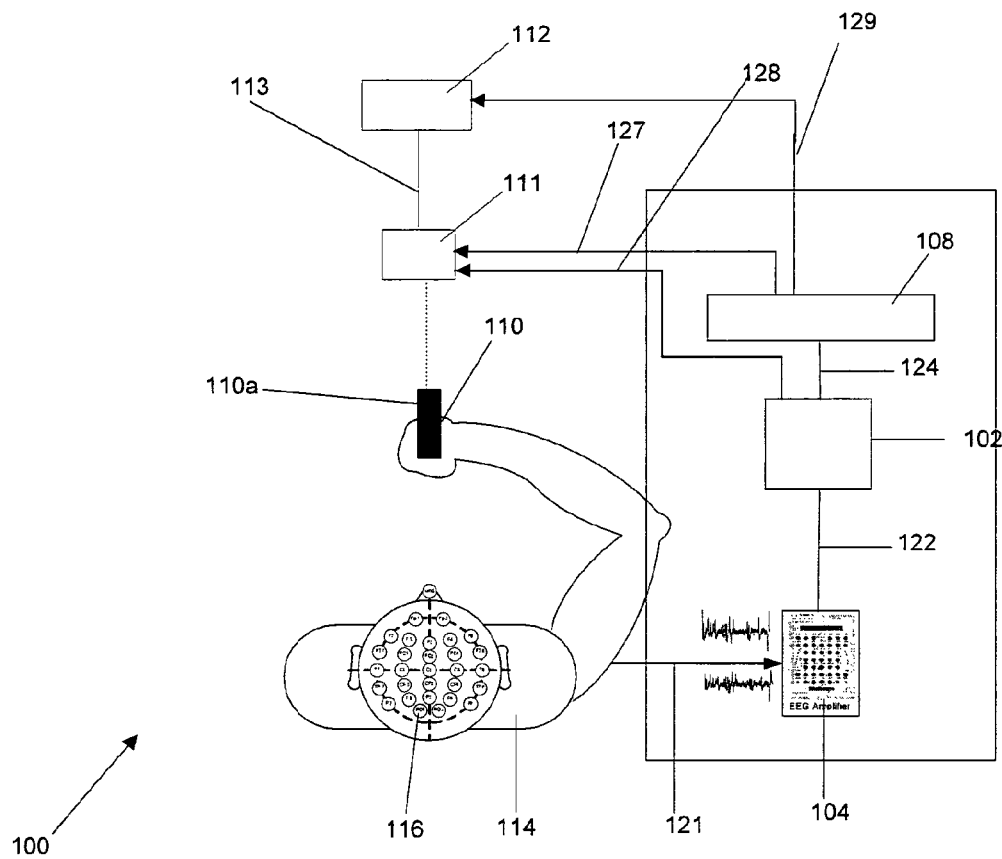
FIG. 1 is a schematic drawing illustrating a system architecture of a non-invasive electroencephalogram (EEG) based brain-computer interface (BCI) for stroke rehabilitation, according to an example embodiment of the present invention.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

FIG. 1 is a schematic drawing illustrating a system architecture, designated generally as reference numeral 100, of a non-invasive electroencephalogram (EEG) based brain-computer interface (BCI) for stroke rehabilitation, according to an example embodiment of the present invention, comprising a motor imagery detection module 102, an EEG amplifier 104, a therapy control module 108, a motion detector device 110, a computer module 111 and a display screen 112. The motion detector device 110 advantageously comprises a stimulation element, here in the form of a vibration motor 110a for providing a stimulus to the patient.

A subject 114 is wearing an EEG cap 116. Signals acquired via the EEG cap 116 are sent to the EEG amplifier 104 via connection 121 for amplification. After amplification, the signals are sent to the motor imagery detection module 102 via connection 122. During calibration, instructions are sent from the motor imagery detection module 102 to the computer module 111 via connection 128. During rehabilitation, motor intent is sent from the motor imagery detection module 102 to the therapy control module 108 via connection 124. The therapy control module 108 is connected to the screen 112 via connection 129 to provide visual feedback to the subject 114. Tactile feedback can also be provided to the patient through the motion detector device 110 via the computer module 111 via connection 128. The motion detector device 110 in is wireless communication with the computer module 111.

For illustrative purposes, one hand-held motion detector device is shown here, however, it will be appreciated by a person skilled in the art that more than one motion detector may be used and the motion detector(s) can be coupled to any limb and/or body part which is undergoing rehabilitation. If the patient is unable to hold a motion detector properly, the motion detector may be "strapped" onto the hand, e.g. using a glove with a velcro patch for attaching the motion detector device using a corresponding patch on the motion detector device.

Embodiments of the present invention advantageously facilitate BCI-based stroke rehabilitation in a home environment and may provide, both visual and tactile feedback to the patient.

Example embodiments advantageously enhance interaction with a patient and provide better feedback on rehabilitation performance by detecting voluntary movements and providing tactile feedback. At the same time, the BCI detects motor imagery action and provides visual feedback. In addition, a predicted motor imagery action can be mapped to both the visual feedback on the BCI and tactile feedback on the motion detectors.

An example of a motion detector device including a stimulation element that may be incorporated into this embodiment is a Wii Remote, the primary controller of a Nintendo Wii game console. The Wii Remote is a wireless device that comprises linear accelerometers for motion detection, a vibration motor to provide tactile feedback, optical sensors and a bluetooth communication system, allowing users to interact with and manipulate items on a screen via gesture recognition and pointing.

Referring back to FIG. 1, calibration of the motor imagery detection module 102 is initially performed. The calibration process described above is discussed in more detail below.

Calibration Phase
Feature Extraction

Figure 2:
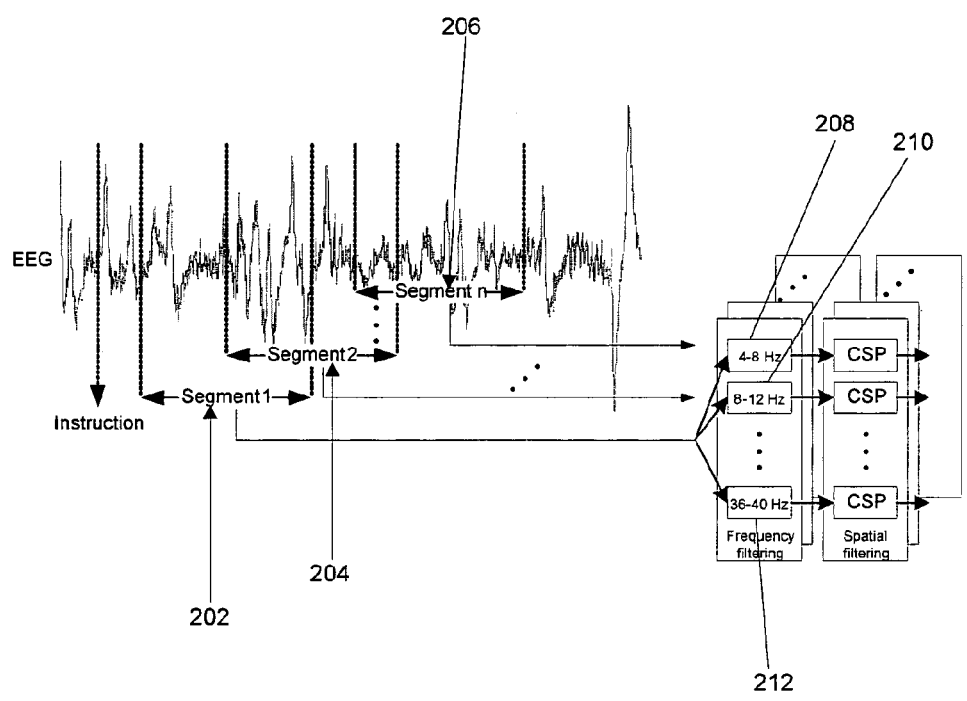
FIG. 2 is an example EEG illustrating the decomposition of the EEG into multiple time segments and frequency banks, according to an example embodiment of the present invention.

The acquired EEG from the subject is decomposed into multiple filter banks and time segments. FIG. 2 is an example EEG, designated generally as reference numeral 200, illustrating the decomposition of the EEG into multiple overlapping time segments (e.g.: 202, 204, 206), according to an example embodiment of the present invention. Data in each time segment is decomposed into multiple (non-overlapping) frequency banks, for example 4-8 Hz (208), 8-12 Hz (210), and 36-40 Hz (212). Thereafter, a Common Spatial Pattern (CSP) algorithm can be employed to extract CSP features from each filter bank and time segment.

The EEG from each time segment and each filter bank can be linearly transformed using $$y = W^T x \qquad (1)$$

where x denotes an n×t matrix of the EEG data; y denotes an n×t matrix of uncorrelated sources; W denotes a n×n time-invariant transformation matrix; n is the number of channels; t is the number of EEG samples per channel; and $^T$ denotes a transpose operator. $W = [w_1, w_2, \ldots, w_3]$ such that each $w_i$ represents a particular spatial filter.

A motor imagery state from a specific frequency band is denoted by $\omega_p$ and the idle state is denoted by $\omega_n$. Multiple motor imagery states from multiple frequency bands are considered at a later stage. The probability of the motor imagery state and the idle state are respectively denoted by $P(\omega_p)$ and $P(\omega_n)$, such that $P(\omega_p) + P(\omega_n) = 1$, and the class conditional probability density functions are respectively denoted by $p(x|\omega_p)$ and $p(x|\omega_n)$ whereby x is a random sample of an EEG measurement. The Bayes error for classifying x into the two classes is given by $$\varepsilon(x) = \int \min[P(\omega_p) p(x|\omega_p), P(\omega_n) p(x|\omega_n)] dx \qquad (2)$$

$$\equiv \int_{R_n} p(x|\omega_p) P(\omega_p) dx + \int_{R_p} p(x|\omega_n) P(\omega_n) dx$$

where $R_p$ is the Bayes decision region in which $p(x|\omega_p)P(\omega_p) > p(x|\omega_n)P(\omega_n)$, and R is the Bayes decision region in which $p(x|\omega_n)P(\omega_n) > p(x|\omega_p)P(\omega_p)$.

The close-form expression for the Bayes error is not easily obtained except in very special cases. Hence the upper bound of the Bayes error is usually obtained instead. The Bhattacharyya bound of equation (2) is given by $$\epsilon_B(x) = \sqrt{P(\omega_p)P(\omega_n)} \int \sqrt{p(x|\omega_p)p(x|\omega_n)} dx \qquad (3)$$

The Bhattacharyya bound $\epsilon_B(y)$ is in the same form as equation (3) except that the variables and the probability density functions are replaced by y and its probability density functions. Therefore, the objective of linear spatial filtering can also be viewed as optimizing the linear projection matrix W to yield the minimal Bhattacharyya bound $\epsilon_B(y)$. Since the Bhattacharyya bound depends on the probability density functions, it can be treated under the uni-modal or multi-modal approaches as described below:

Uni-Modal Approach

Let $p(x|\omega)$ and $p(x|\omega_p)$ be modeled by uni-modal Gaussian functions with covariance matrices $\psi_p$ and $\psi_n$ respectively. Further assume that the EEG is band-pass filtered, in which the mean of both classes is assumed to be zero. The probability density functions can then be modeled as $$p(x|\omega_p) \sim N(0, \psi_p) \sim (2\pi)^{-\frac{n_c}{2}} |\psi_p|^{-\frac{1}{2}} \exp\left(-\frac{1}{2} x^T \psi_p^{-1} x\right), \qquad (4)$$

and $$p(x|\omega_n) \sim (2\pi)^{-\frac{n_c}{2}} |\psi_n|^{-\frac{1}{2}} \exp\left(-\frac{1}{2} x^T \psi_n^{-1} x\right), \qquad (5)$$

where $n_c$ is the number of dimensions or channels of $\omega_p$ and $\omega_n$.

The Bhattacharyya bound is thus given by $$\varepsilon_B = \sqrt{P(\omega_p)P(\omega_n)} \exp\left(\frac{1}{2}\log\frac{\left|\frac{\psi_p + \psi_n}{2}\right|}{\sqrt{|\psi_p||\psi_n|}}\right), \quad (6)$$

where $|\cdot|$ denotes the determinant of a square matrix.

The Bhattacharyya bound after spatial filtering using W can be written in a similar form by replacing the covariance matrices with that from the transformed data using $\psi_p(y)=W^T\psi_p$ and $\psi_n(y)=W^T\psi_n W$. The closed-form solution to minimizing the Bhattacharyya bound with respect to W can then be obtained. Given a particular selection of m, the optimum W is the collection of top m eigenvectors of $\psi_n^{-1}\psi_p$, or $$\psi_p w_i = \lambda_i \psi_n w_i, \quad (7)$$

where $\lambda_i$ is the ith eigenvalue and $w_i$ the corresponding eigenvector. The eigenvectors obtained correspond to the common spatial pattern (CSP) algorithm that is widely used by motor imagery-based BCIs and understood in the art.

Multi-Modal Approach

The detection of the idle state in which the user is at rest and not performing mental control is crucial in minimizing false positive detections in asynchronous BCIs. The inclusion of the idle state has been experimentally shown to improve the accuracy of the asynchronous BCIs. In embodiments of the present invention, the multi-modal approach of modeling the idle states in asynchronous motor imagery-based BCIs is performed using the framework of the Bhattacharyya bound.

Figure 3:
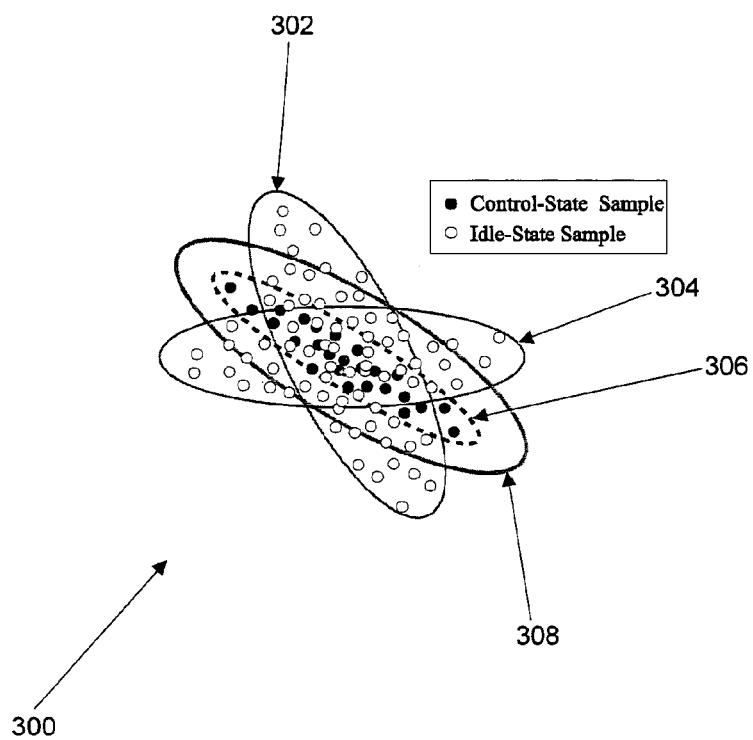
FIG. 3 illustrates the difference between a multi-modal approach and a uni-modal approach in picking up discriminative spatial patterns.

Some advantages of adopting the multi-modal approach are as follows:
1. From the brain signal viewpoint, the idle state comprises multiple manifestations of all possible EEG patterns other than those that are associated with control motor imagery states. Since the user can be performing any mental activity other than those of the control motor imagery tasks in the idle state, the EEG measurements of the idle state is largely diversified in terms of spatio-spectral characteristics. Therefore, a multi-modal approach preferably is more appropriate to model the idle state compared to the unimodal approach.
2. From the linear transformation viewpoint, the optimum spatial filters that assume the uni-modal approach may fail to pick up discriminative spatial patterns. FIG. 3, designated generally as reference numeral 300, illustrates the difference between a multi-modal approach and a uni-modal approach in picking up discriminative spatial patterns. Using the multi-modal approach, idle states 302 and 304 exhibit distinguishing spatial directions that are different from control state 306. In contrast, using the uni-modal approach, idle state 308 is similar to the control state 306.

Let the idle state $\omega_n$ be modeled by M sub-classes $\chi_j=1, \ldots, M$. The prior probability of each sub-class is denoted by $\tilde{P}(\chi_j)$ such that $\Sigma_{j=1}^M \tilde{P}(\chi_j)=1$. Assume that each sub-class is modeled by a Gaussian distribution function with zero-mean and covariance matrix $\tilde{\psi}_j$. Hence, the distribution of the idle state $\omega_n$ can be expressed as a Gaussian mixture model given by $$p(x|\omega_n) \sim \qquad (8)$$

$$\sum_{j=1}^M \tilde{P}(\chi_j)N(0, \tilde{\psi}_j) \sim (2\pi)^{-\frac{n_c}{2}} \sum_{j=1}^M \tilde{P}(\chi_j)|\tilde{\psi}_j|^{-\frac{1}{2}} \exp\left(-\frac{1}{2}x^T\tilde{\psi}_j^{-1}x\right).$$

After spatial filtering using the linear transformation W, the motor imagery state $P(\omega_p)$ and the idle state $P(\omega_n)$ are still Gaussian distributions. Hence the distributions of the motor imagery states $P(\omega_p)$ and the idle state $P(\omega_n)$ can be expressed as $$p(y|\omega_p) \sim N(0, \psi_{p(y)}), \quad (9)$$

$$p(y|\omega_n) \sim \sum_{j=1}^M \tilde{P}(\chi_j)N(0, \tilde{\psi}_{j(y)}), \quad (10)$$

where $$\psi_{p(y)} = W^T \psi_p W, \quad (11)$$

$$\tilde{\psi}_{j(y)} = W^T \tilde{\psi}_j W, \quad (12)$$

and the Bhattacharyya bound is given by $$\epsilon_B(y) = \sqrt{P(\omega_p)P(\omega_n)} \int \sqrt{p(y|\omega_p)p(y|\omega_n)}\,dy \quad (13)$$

It will be appreciated that it is difficult to compute the Bhattacharyya bound in equation (13), hence, an approximate numerical solution can be found instead. Ignoring the constant factor $\sqrt{P(\omega_p)P(\omega_n)}$, the Bhattacharyya coefficient that comprises the integral in equation (13) can be expressed as $$\mu = \int \sqrt{p(y|\omega_p)p(y|\omega_n)}\,dy \quad (14)$$

$$\equiv \int \mu_1(y)\mu_2(y)\,dy,$$

where $$\mu_1(y) = \sqrt{p(y|\omega_p)} \text{ and } \mu_2(y) = \sqrt{p(y|\omega_n)}.$$

Expanding $\mu_1(y)$ in the form that is similar to equation (5) gives $$\mu_1(y) = \sqrt{(2\pi)^{-\frac{n_c}{2}}|\psi_{p(y)}|^{-\frac{1}{2}}\exp\left(-\frac{1}{2}y^T\psi_{p(y)}^{-1}y\right)} \quad (15)$$

$$= \left\{(2\pi)^{-\frac{n_c}{2}}|2\psi_{p(y)}|^{-\frac{1}{2}}\exp\left(-\frac{1}{2}y^T(2\psi_{p(y)})^{-1}y\right)\right\} \cdot$$

$$\left\{(2\pi)^{\frac{n_c}{4}}2^{\frac{n_c}{2}}|\psi_{p(y)}|^{\frac{1}{4}}\right\}$$

The expression in the first curly bracket { } can be viewed as a probability density function $$P(y) = N(0, 2\psi_{p(y)}), \quad (16)$$

and the expression in the second curly bracket { } can be written with $\mu_2(y)$ as $$Q(y) = (2\pi)^{\frac{n_c}{4}} 2^{\frac{n_c}{2}} |\psi_{p(y)}|^{\frac{1}{4}} \cdot \sqrt{\sum_{j=1}^{M} \tilde{P}(\chi_j) N(0, \tilde{\psi}_{j(y)})}. \quad (17)$$

Therefore, the Bhattacharyya coefficient can be expressed as $$\mu = \int P(y) Q(y) dy. \quad (18)$$

Since P(y) is a probability distribution function, the Bhattacharyya coefficient can be expressed as the expectation of Q given by $$\mu = E[Q(y)], \quad (19)$$

where $$p(y|\omega_p) \sim N(0, 2W^T \psi_p W). \quad (20)$$

The variable y in equation (20) is obtained by transforming the variable x in the original space using W whereby $$p(x|\omega_p) \sim N(0, 2\psi_p). \quad (21)$$

It is assumed that $p(x_i|\omega_p) \sim N(0, \omega_p)$, $i=1, \ldots, n_p$ from equation (5). Hence to have $\hat{x}$ that follows the distribution in equation (21), $$p(\sqrt{2}\hat{x}_i|\omega_p) \sim N(0, 2\omega_p), i=1, \ldots, n_p, \quad (22)$$

and therefore $$\mu = \lim_{n_p \to \infty} \frac{1}{n_p} \sum_{i=1}^{n_p} Q(W^T \sqrt{2} \hat{x}_i) \quad (23)$$

It will be appreciated that equation (23) is a relatively complex function over W while the global optimum is difficult to achieve. A simplified problem of searching for the optimum W among a given set of candidates is preferably performed as follows:

Let the candidate set be $K_{cand}$, which consists of $n_{cand}$ vectors. Consider a subset K that contains $n_{sel}$ selected vectors. The transformation matrix formed by the subset K is bf$W_K$. The problem is then formulated to search for the optimum set $K_{opt}$ that satisfies $$K_{opt} = \operatorname{argmin}_{K} \frac{1}{n_p} \sum_{i=1}^{n_p} Q(W_K^T \sqrt{2} \hat{x}_i) \quad (24)$$

In embodiments of the present invention, a small $K_{cand}$ is considered so that it is computationally feasible to enumerate all possible combinations of selecting $n_{sel}$ from $n_{cand}$. The following algorithm is preferably used to obtain hcal$K_{cand}$ and $K_{opt}$:
1. $K_{cand} = \%$;
2. For each idle state subclass m:
   a. Compute the projection matrices $W_m$ that maximizes the Bhattacharyya distance between the idle state subclass m and the motor imagery class, by solving the eigen problem given in equation (7).
   b. Select from $W_m$ the linear projection vectors which produce the least Bhattacharyya coefficient $$\lambda_i + \frac{1}{\lambda_i}, \quad (25)$$

where $\lambda_i$ is the eigen value.

c. The set of selected vectors from $W_m$ for the idle state m is denoted as $K_m$.
  d. $K_{cand} \cup K_m \to K_{cand}$;
3. Enumerate all $n_{sel}$-sized subsets of $K_{cand}$, and compute the estimate of Bhattacharyya coefficient using equation (23) for each subset;
4. Select the subset $K_{opt}$ which satisfies equation (24).

Feature Selection

The optimal transformation W obtained above is preferably integrated into a Filter Bank Common Spatial Pattern algorithm (FBCSP) (as disclosed by Ang et al, Filter Bank Common Spatial Pattern (FBCSP) in Brain-Computer Interface. Proc. IJCNN'08, 2391-2398) which deals with multiple classes involving multiple motor imagery classes and the idle state class, as well as multiple frequency bands for motor imagery detection.

The variances of only a small number m of the spatial filtered signal Z(t) by the FBCSP algorithm are used as features. Signal $Z_p(t)$, $p \in \{1 \ldots 2m\}$ that maximizes the difference in the variance of the two classes of EEG are associated with the largest eigenvalues $\lambda$ and $(I-\lambda)$. These signals are used to form feature vector $X_p$ for each time segment and each filter bank.

$$X_p = \log\left(\operatorname{var}(Z_p(t)) \Big/ \sum_{i=1}^{2m} \operatorname{var}(Z_p(t))\right) \quad (26)$$

Feature selection is advantageously performed using Mutual Information. Assuming a total of d features from each time segment $F=\{f_1, f_2, \ldots f_d\}$, the Mutual Information $I(f_i; \Omega) \forall i=1 \ldots d$, $f_i \in F$ of each feature is computed from all the time segments and all the filter banks with respect to the class $\Omega$.

A set of k=4 features is selected in the example embodiment from each time segment that maximizes $I(f_i; \Omega)$ using $$F = F \setminus \{f_i\}, S = \{f_i\} \mid I(f_i; \Omega) = \max_{j=1 \ldots d, f_j \in F} I(f_j; \Omega). \quad (27)$$

The mutual information of the k=4 features from each time segment is then summed together. The time segment with the maximum sum of mutual information is selected. It will be appreciated that different values of k may be used in different embodiments.

For instance, there may be 9 FBCSP projection matrices (W), one projection matrix for each of 9 frequency bands in one example embodiment. Once the time segment has been selected as described above, the features of each frequency band are evaluated to determine which frequency band is selected. In this example, where k=4, a minimum of 1 and a maximum of 4 frequency bands and associated FCSB matrices are selected, depending on whether the whether the features with the highest mutual information are determined to be from the same or from different frequency bands. The projection matrix/matrices W from the selected time segment and frequency band/bands and the features of the selected frequency band/bands are retained.

Non-Linear Regression

A patient may perform more than one trial. Features from respective trials are computed using the projection matrix/matrices (W) from the selected time segment and frequency band/bands. The extracted features from all the trials belonging to the selected time segment and frequency band/bands are also retained as training features for the non-linear regression while the features from the non selected time segment and frequency bands are dropped. The selected features are then linearly normalized to the range [−1 1] using the upper and lower bounds of the training set features, which can advantageously provide for detection of level of motor intent in addition to detection of class of motor intent in the example embodiment. To map the features to the desired outputs, a generalized regression neural network (GRNN) is used. The network preferably comprises of two layers of neurons. The first layer comprises radial basis function neurons, while the second layer comprises linear neurons with normalized inputs.

Post Processing

Another GRNN can be used to perform post-processing. The input of the neural network is a window of predicted labels obtained from the non-linear regression, while the output is the desired output.

Figure 4:
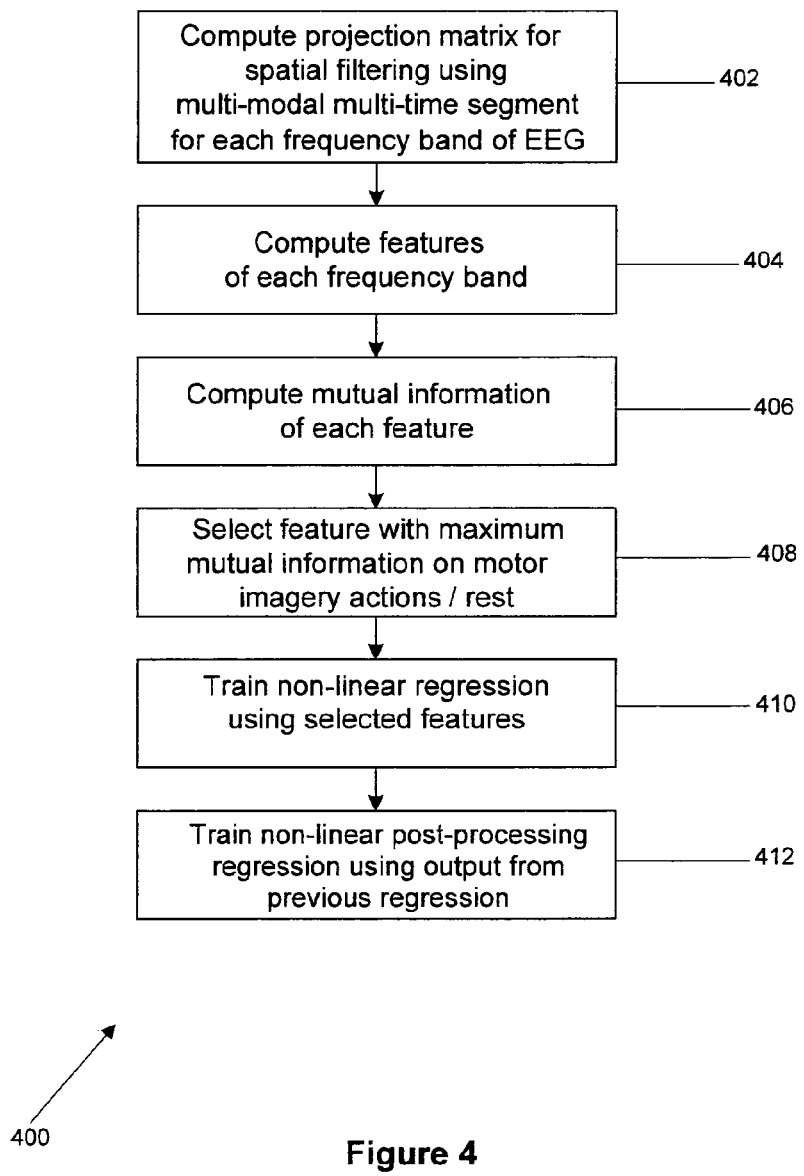
FIG. 4 is a flowchart summarizing the steps in a calibration phase, according to an embodiment of the present invention.

FIG. 4 is a flowchart, designated generally as reference numeral 400, summarizing the steps in a calibration phase, according to an embodiment of the present invention. At step 402, a projection matrix is computed for spatial filtering using multi-modal multi-time segment for each frequency band of EEG. At step 404, features of each frequency band are computed. At step 406, mutual information of each feature is computed. At step 408, features with maximum mutual information on motor imagery actions and rest are selected. At step 410, selected features are trained using non-linear regression. At step 412, post processing is performed using non-linear regression from the output obtained from step 410.

Rehabilitation Phase

With reference back to FIG. 1, after calibration is completed, rehabilitation can be performed using the calibrated motor imagery detection module 104 and the therapy control module 108.

After calibration is completed, the subject-specific motor imagery detection module 104 can perform real time detection of the motor intent of the patient. Based on the features selected during the calibration phase, spatial filtering is performed using the projection matrix W on the acquired EEG data. The trained non-linear regression and post processing using GRNN is then used to compute a motor intent output, including a class and a level of motor intent in the example embodiment. The detected class of motor intent is used to provide tactile feedback and the detected class and level of motor intent is used to provide visual feedback to the patient.

It is to be noted that the above described calibration phase may be useful for synchronous systems, some examples of which will be discussed with reference to FIGS. 6 to 9. However, the described calibration phase is also advantageously useful in the implementation of asynchronous rehabilitation systems.

Figure 5:
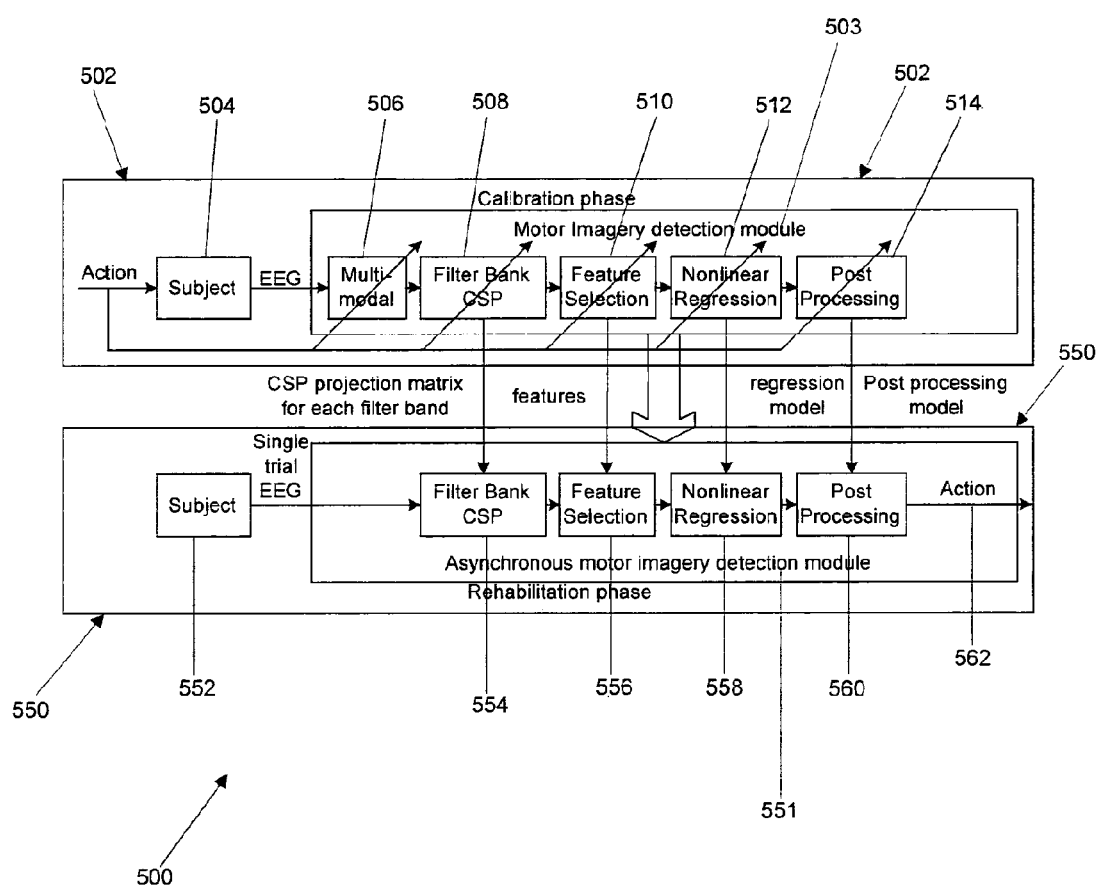
FIG. 5 is a schematic diagram illustrating a calibration phase and an asynchronous motor imagery rehabilitation phase, according to one embodiment of the present invention.

FIG. 5 shows a schematic diagram 500, illustrating a calibration phase, generally designated as reference numeral 502, and an asynchronous motor imagery rehabilitation phase, generally designated as reference numeral 550, according to one embodiment of the present invention.

During the calibration phase 502, a motor imagery detection module 503, comprising a multi-modal processing unit 506, a CSP filter bank unit 508, a feature selection unit 510, a non-linear regression processing unit 512 and a post-processing regression unit 514, is used for calibration as described above with reference to FIGS. 2 to 4. Subsequently, the calibrated imagery detection module functions as an asynchronous motor imagery detection module 551 during the asynchronous motor imagery rehabilitation phase 550.

During asynchronous motor imagery rehabilitation 550, the asynchronous motor imagery detection module 551, comprising a calibrated CSP filter bank unit 554, a calibrated feature selection unit 556, a calibrated non-linear regression processing unit 558 and a calibrated post-processing regression unit 560, is used for asynchronous motor imagery detection based on EEG signals acquired from a person. It will be appreciated by a person skilled in the art that rehabilitation is advantageously not driven by a rehabilitation algorithm (i.e.: cue-based), but is driven by a person undergoing rehabilitation based on his motor imagery. This may be an alternative, or an addition, to asynchronous initiation of a rehabilitation phase through actual movement of the relevant limb by the person.

Asynchronous BCI-robotic rehabilitation, according to embodiments of the present invention, advantageously allows patients to perform a motor intent whenever the patient wishes. Detection in an asynchronous manner advantageously does not require the user to time his/her motor imagery and mental effort relative to a cue, making rehabilitation more patient-friendly.

On the other hand, in the following description, example embodiments of cue-based (i.e.: synchronous) rehabilitation using the system architecture 100 of FIG. 1 and the calibration phase described above with reference to FIGS. 2 to 4 will be described.

Figure 6:
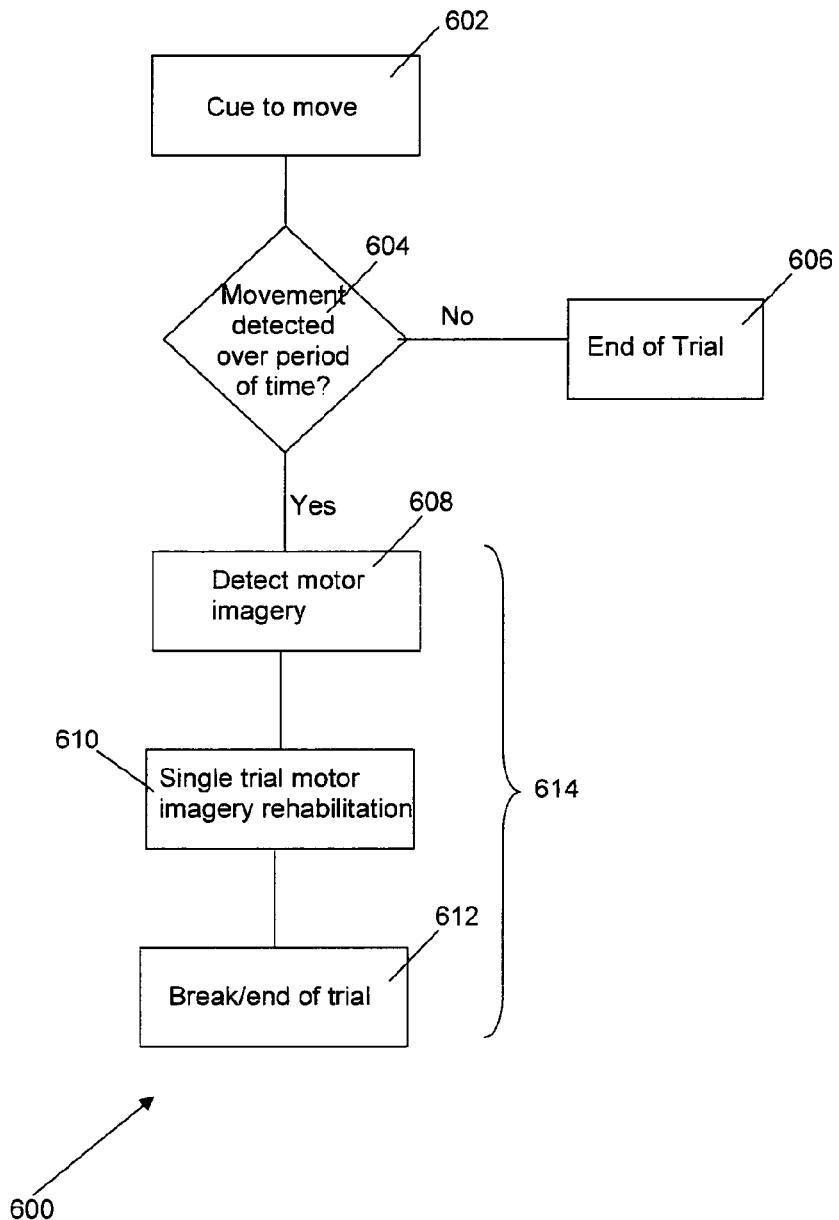
FIG. 6 is flowchart illustrating steps for a single trial in a BCI system, according to an embodiment of the present invention.

FIG. 6 is a flowchart, designated generally as reference numeral 600, illustrating steps for a single trial in a BCI system, according to an embodiment of the present invention. At step 602, a user is given a cue to move, for example, his right hand. At step 604, the BCI system detects if a movement is detected over a certain period of time. If no movement is detected over the certain period of time, the trial ends at step 606. If movement is detected within the certain period of time, detection of motor imagery is carried out at step 608. At step 610, single trial motor imagery rehabilitation is carried out. Upon completion of rehabilitation, the trial ends at step 612. A break period can be provided before the next trial. The motor imagery detection and rehabilitation portion of the trial is designated as reference numeral 614 and an example implementation for motor imagery detection and rehabilitation will be described with reference to FIG. 7.

Figure 7:
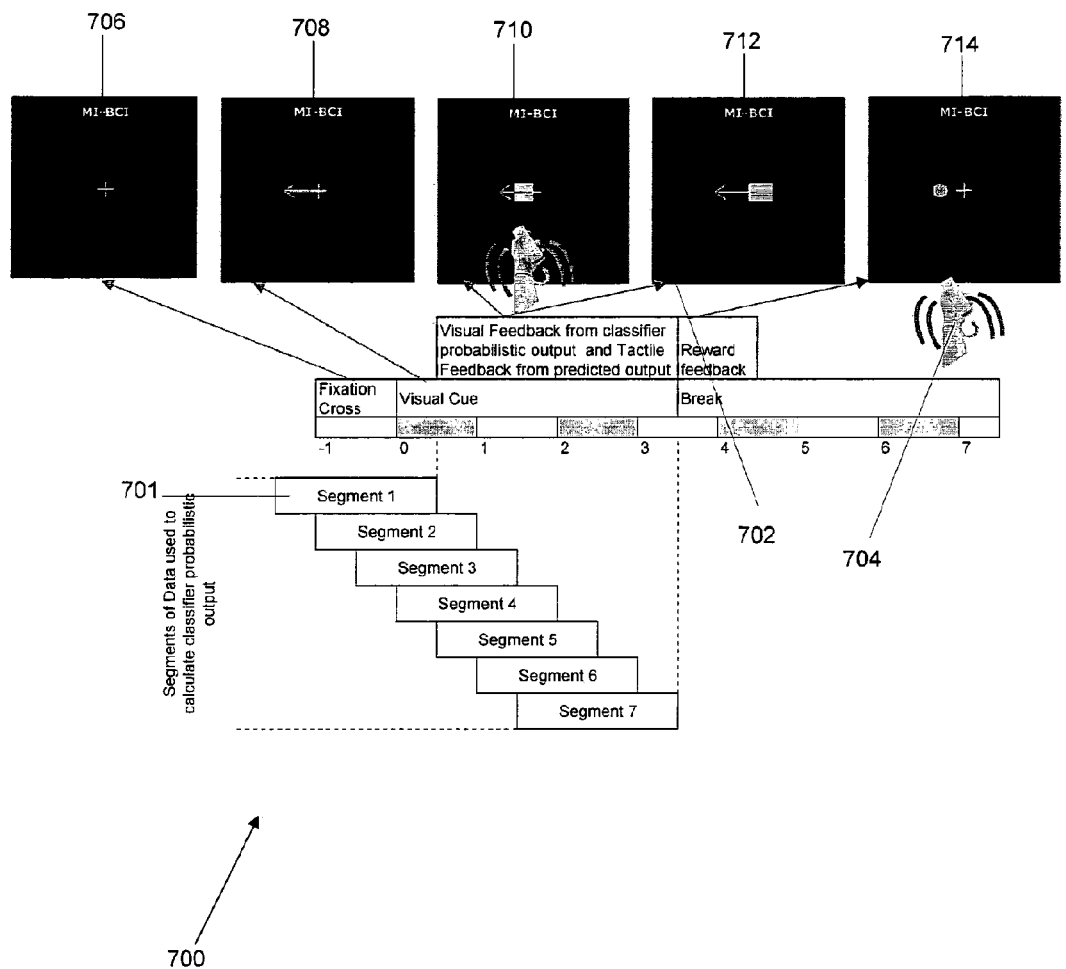
FIG. 7 is a time-line illustrating a sequence of events during a motor imagery detection and rehabilitation phase, according to an embodiment of the present invention.

FIG. 7 is a time-line, designated generally as reference numeral 700, illustrating a sequence of events during a motor imagery detection and rehabilitation phase, according to an embodiment of the present invention. FIG. 7 also shows screen capture images that may be displayed on a screen at different time intervals. Initially, a fixation cross is displayed, illustrated by screen capture 706. A moving window (a segment, e.g.: 701), is used to compute the classifier probabilistic output from the motor imagery detection module (refer to FIG. 1), which can be used to provide performance feedback to the user. A visual cue, here in the form of a left-pointing arrow (see screen capture 708), is displayed to prompt the user to move his hand to the left. If the user performs the correct motor imagery to move his hand to the left, tactile feedback 702 and visual feedback is provided (see screen capture 710, where a box is displayed moving in the correct direction corresponding to the arrow). Within each segment during rehabilitation, if the user performs a correct motor imagery, visual and tactile feedback is provided. If the user ceases to perform the correct motor imagery to move his hand to the left, no tactile feedback is provided, but a visual feedback indicates the incorrect motor imagery (see screen capture 712, where the box is displayed moving in the direction opposite to the arrow). When the trial ends and a break period is provided, if the user performed the correct motor imagery for more than half of the time during the trial, a tactile reward feedback 704 and a visual reward 714 are provided.

In the description above with reference to FIGS. 6 and 7, detection of movement triggers the detection of motor imagery. However, many other configurations are possible, as will be appreciated. For example, as will be described below, detection of correct motor imagery can trigger the detection of movement in the BCI system.

Figure 8:
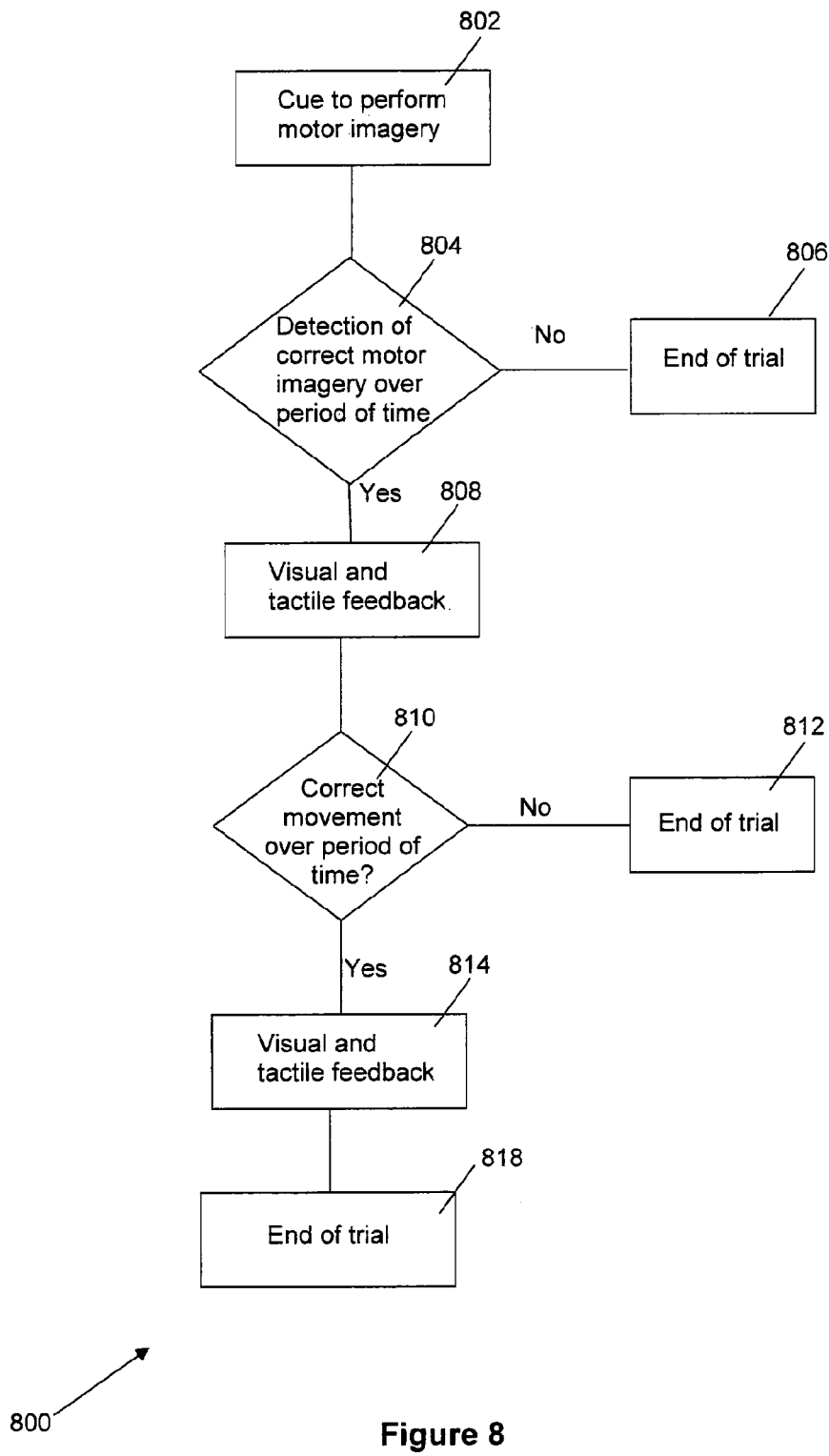
FIG. 8 is a flowchart illustrating steps for a single trial in a BCI system, according to another embodiment of the present invention.

FIG. 8 is a flowchart, designated generally as reference numeral 800, illustrating steps for a single trial in a BCI system, according to another embodiment of the present invention. At step 802, a user is given a cue to perform a certain motor imagery (e.g.: move hand up). At step 804, the BCI system detects if the correct motor imagery is presented by the user within a certain period of time. If no correct motor imagery is detected within the certain period of time, the trial ends at step 806. If correct motor imagery is detected within the certain period of time, visual and tactile feedback is provided at step 808. At step 810, the system detects if a correct movement (i.e.: hand is moved up) is detected over a certain period of time. If no correct movement is detected over the certain period of time, the trial ends at step 812. If the correct movement is detected within the certain period of time, visual and tactile feedback is provided at step. At step 818, the trial ends.

Figure 9:
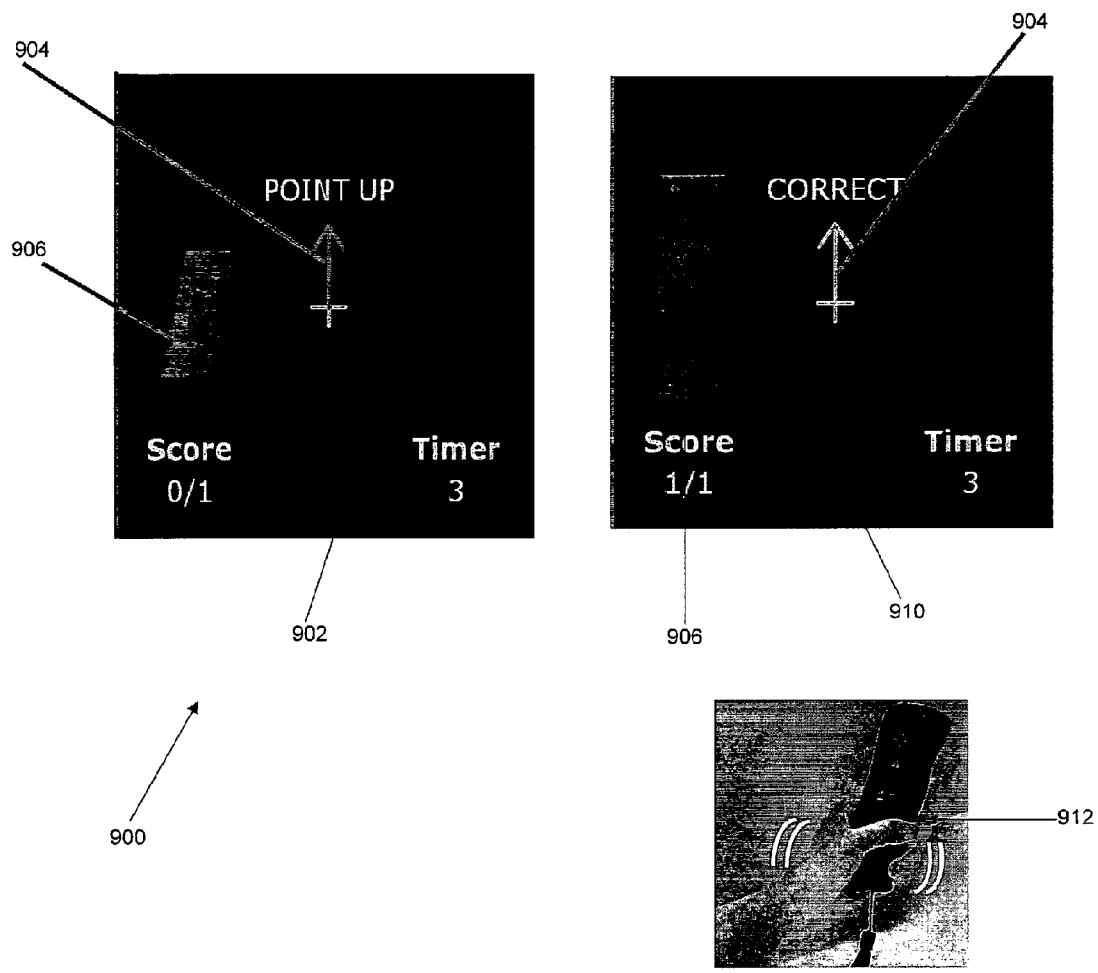
FIG. 9 is a screen capture of an on-screen user interface, illustrating the feedback provided in an example trial as described with reference to FIG. 8.

FIG. 9 is a screen capture, designated generally as reference numeral 900, of an on-screen user interface, illustrating the feedback provided in an example trial as described above with reference to FIG. 8. In screen 902, the graphical user interface displays an arrow 904 pointing up, prompting a user to move his hand up. A virtual motion detector 906 may be displayed on the screen to provide another form of visual aid. In screen 910, when the user correctly moves the motion detector up, 2 types of positive feedback are provided—tactile feedback from a motion detector device 912 and visual feedback (the arrow 904 changes colour and the virtual motion detector 906 moves up).

The addition of a motion detector to enable another facet of interaction and feedback to the existing BCI advantageously allows users with different degrees of limb mobility to interact with the rehabilitation system. Users with higher degree of motor capability may perform cue-based voluntary motion detector movements and perform motor imagery while users with little or no capability of movement may employ only motor imagery.

Figure 10:
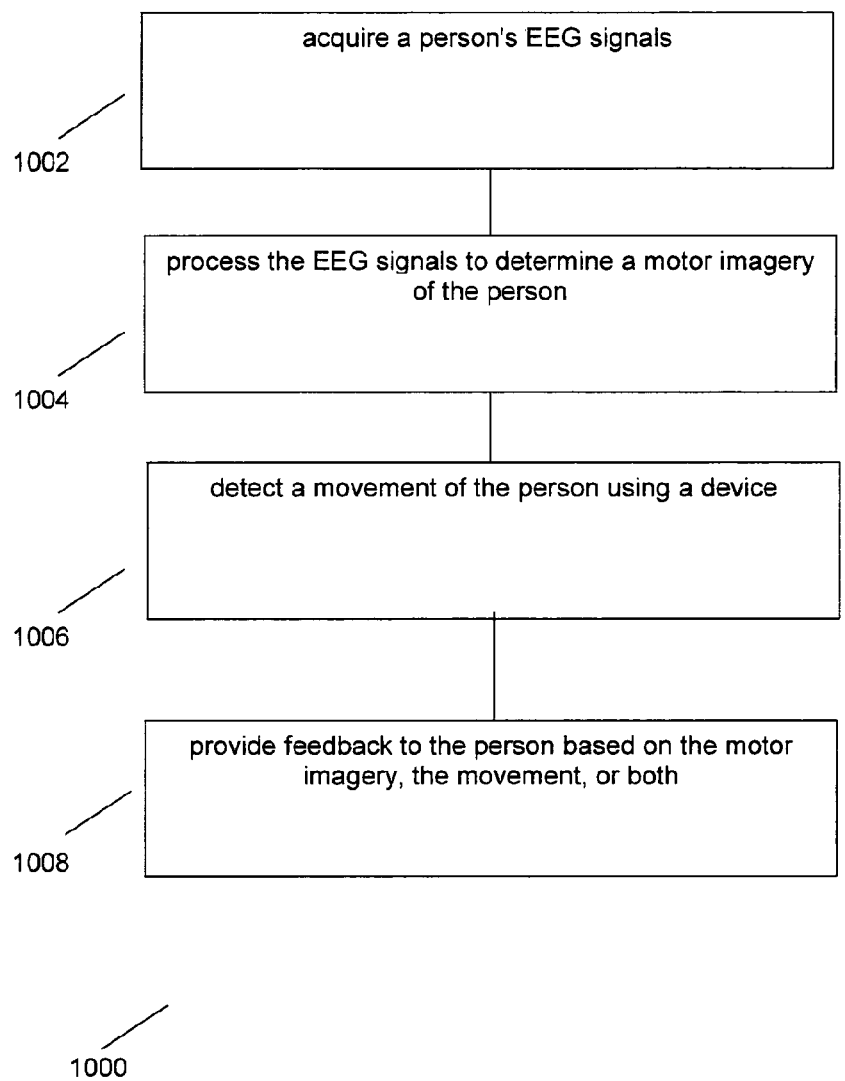
FIG. 10 is a flow chart illustrating the steps of a method for brain-computer interface based interaction, according to an example embodiment of the present invention.

FIG. 10 is a flow chart, designated generally as reference numeral 1000, illustrating the steps of a method for brain-computer interface based interaction, according to an example embodiment of the present invention. At step 1002, a person's EEG signal is acquired. At step 1004, the EEG signal is processed to determine a motor imagery of the person. At step 1006, a movement of the person is detected using a detection device. At step 1008, feedback is provided to the person based on the motor imagery, the movement, or both; wherein providing the feedback comprises activating a stimulation element of the detection device for providing a stimulus to the person.

Figure 11:
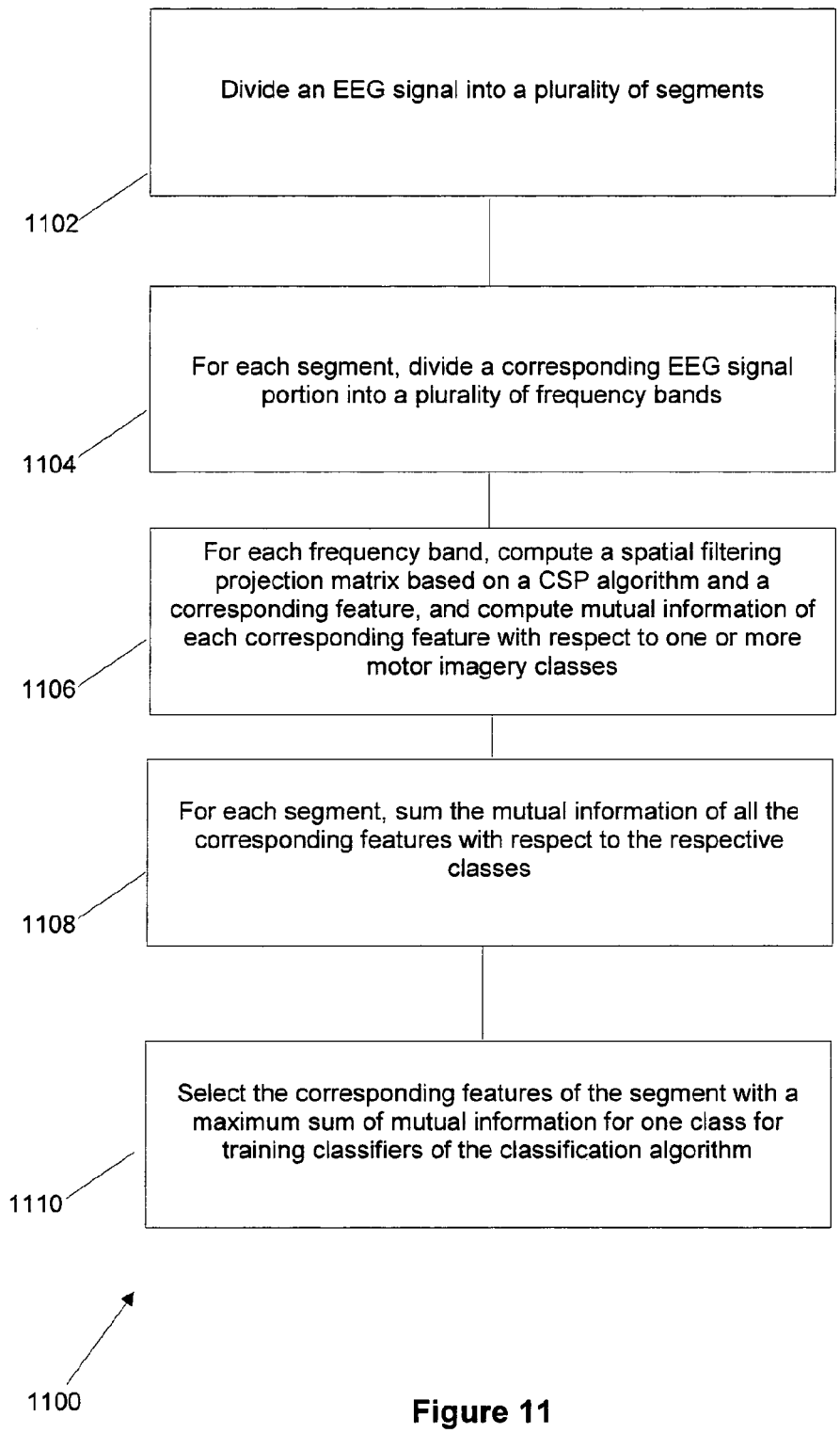
FIG. 11 is a flow chart illustrating a method of training a classification algorithm for a BCI, according to an example embodiment of the present invention.

FIG. 11 is a flow chart, designated generally as reference numeral 1100, illustrating the steps of a method of training a classification algorithm for a BCI according to an example embodiment of the present invention. At step 1102, an EEG signal is divided into a plurality of segments. At step 1104, for each segment, a corresponding EEG signal portion is divided into a plurality of frequency bands. At step 1106, for each frequency band, a spatial filtering projection matrix is computed based on a CSP algorithm and a corresponding feature, and mutual information of each corresponding feature is computed with respect to one or more motor imagery classes. At step 1108, for each segment, the mutual information of all the corresponding features is summed with respect to the respective classes. At step 1110, the corresponding features of the segment with a maximum sum of mutual information for one class are selected for training classifiers of the classification algorithm.

Figure 12:
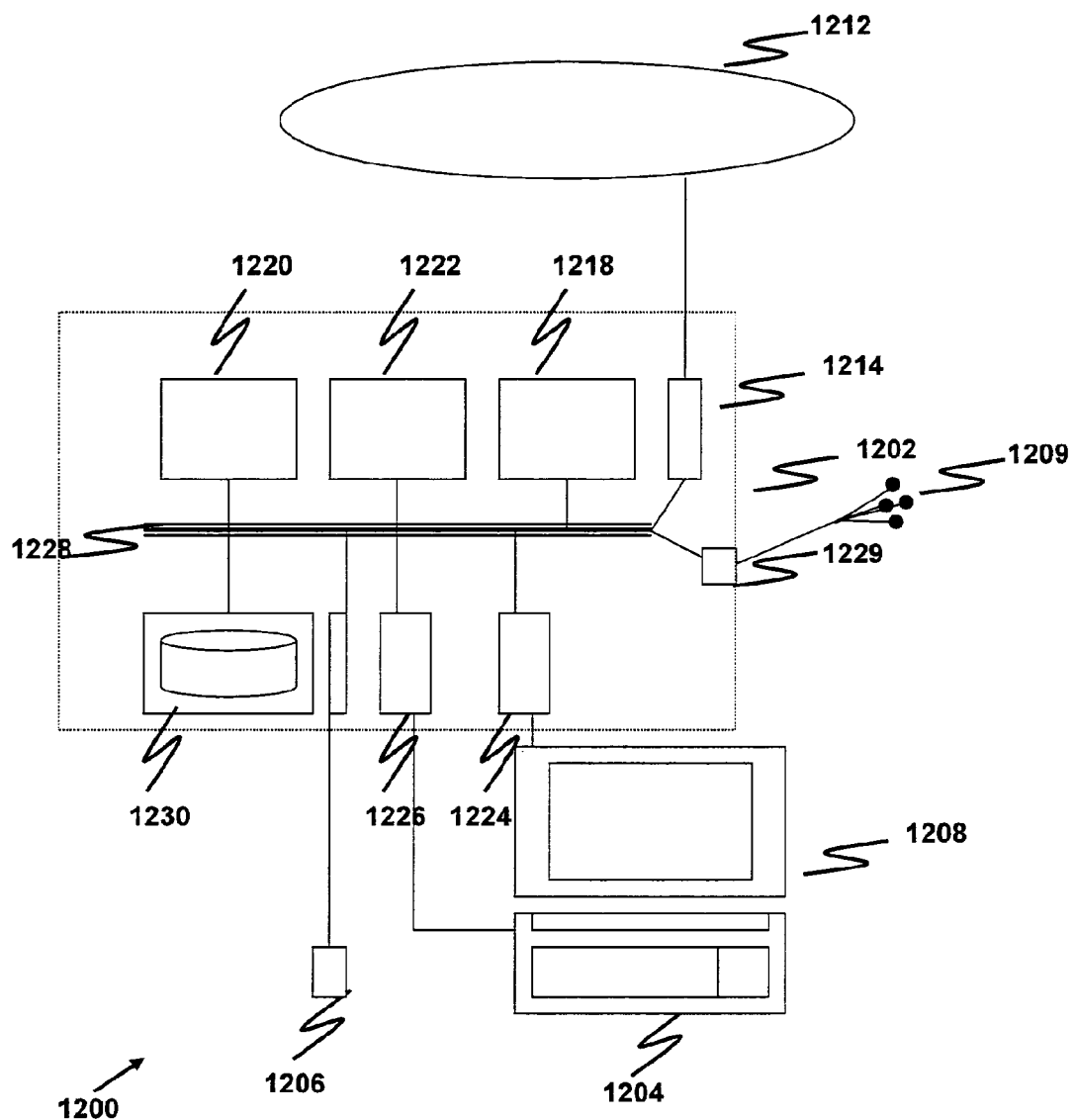
FIG. 12 is a schematic of a computer system for implementing the non-invasive EEG-based brain-computer interface in example embodiments.

The method and system of the example embodiment can be implemented on the computer system 1200, schematically shown in FIG. 12. It may be implemented as software, such as a computer program being executed within the computer system 1200, and instructing the computer system 1200 to conduct the method of the example embodiment.

The computer system 1200 comprises a computer module 1202, input modules such as a keyboard 1204 and mouse 1206 and a plurality of output devices such as a display 1208 and motion detector device 1209.

The computer module 1202 is connected to a computer network 1212 via a suitable transceiver device 1214, to enable access to e.g. the Internet or other network systems such as Local Area Network (LAN) or Wide Area Network (WAN).

The computer module 1202 in the example includes a processor 1218, a Random Access Memory (RAM) 1220 and a Read Only Memory (ROM) 1222. The computer module 1202 also includes a number of Input/Output (I/O) interfaces, for example I/O interface 1224 to the display 1208, I/O interface 1226 to the keyboard 1204, and I/O interface 1229 to the motion detector device 1209.

The components of the computer module 1202 typically communicate via an interconnected bus 1228 and in a manner known to the person skilled in the relevant art.

The application program is typically supplied to the user of the computer system 1200 encoded on a data storage medium such as a CD-ROM or flash memory carrier and read utilizing a corresponding data storage medium drive of a data storage device 1230. The application program is read and controlled in its execution by the processor 1218. Intermediate storage of program data maybe accomplished using RAM 1220.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

The invention claimed is:

1. A method of training a classification algorithm for a Brain Computer Interface (BCI), the method comprising the steps of:

dividing an Electroencephalography (EEG) signal into a plurality of time segments, for each time segment, dividing a corresponding EEG signal portion into a plurality of frequency bands;

for each frequency band, computing a spatial filtering projection matrix based on a Common Spatial Pattern (CSP) algorithm and a corresponding feature, and computing mutual information of each corresponding feature with respect to one or more motor imagery classes;

for each time segment, summing the mutual information of all the corresponding features with respect to the respective classes;

selecting the corresponding features of each time segment with a maximum sum of mutual information for one class for training classifiers of the classification algorithm; and storing the selected corresponding features of the time segments in a computer system of the BCI, wherein said BCI is configured to determine motor imagery of a person by using said stored selected corresponding features in motor imagery detection.

2. The method as claimed in claim 1, wherein training the classifiers comprises non-linear regression using the selected corresponding features after the corresponding features have been selected by the trained classification and non-linear post-processing regression using an output from the non-linear regression.

3. The method as claimed in claim 1, wherein computing the spatial filtering projection matrix based on the CSP algorithm comprises using a multi-modal multi-time segment for each frequency band.

4. The method as claimed in claim 3, wherein the multi-modal multi-time segment for each frequency band comprises a multi-modal representation of an idle state.

5. A method for brain-computer interface (BCI) based interaction, the method comprising the steps of:
acquiring a person's EEG signal;
processing the EEG signal to determine a motor imagery of the person;
detecting a movement of the person using a detection device; and
providing feedback to the person based on the motor imagery, the movement, or both;
wherein providing the feedback comprises activating a stimulation element of the detection device for providing a stimulus to the person;
wherein the processing of the EEG signal comprises using a trained classification algorithm trained according to claim 1.

6. The method as claimed in claim 5, comprising:
processing the EEG signal to determine whether a specific motor imagery is performed by the person; and
activating the stimulation element based on the specific motor imagery performed.

7. The method as claimed in claim 6, wherein the feedback further comprises a separate visual feedback to the person based on the specific motor imagery performed.

8. The method as claimed in claim 5, comprising:
determining whether a specific movement is performed by the person; and
activating the stimulation element based on the motor imagery of the person.

9. The method as claimed in claim 8, wherein the feedback further comprises a separate visual feedback to the person based on the motor imagery performed.

10. The method as claimed in claim 8, wherein the determining whether the specific movement is performed by the person occurs over a specific period of time.

11. A brain-computer interface (BCI) system comprising:
an Electroencephalography (EEG) device for acquiring a person's EEG signal;
a motor imagery detection module configured for processing the EEG signal and determining a motor imagery of the person;
a motion detector device configured for detecting a movement of the person and providing feedback to the person based on the motor imagery, the movement, or both;
wherein the motion detector device comprises a stimulation element configured for providing a stimulus to the person;
wherein the motor imagery detection module is configured to use a trained classification algorithm; and
wherein to train the classification algorithm, the system is further configured to execute the following steps:
divide the EEG signal into a plurality of time segments;
for each time segment, divide a corresponding EEG signal portion into a plurality of frequency bands;
for each frequency band, compute a spatial filtering projection matrix based on a CSP algorithm and a corresponding feature, and compute mutual information of each corresponding feature with respect to one or more motor imagery classes;
for each time segment, sum the mutual information of all the corresponding features with respect to the respective classes;
select the corresponding features of the time segment with a maximum sum of mutual information for one class for training classifiers of the classification algorithm; and
store the selected corresponding features of the time segments in a computer system of the BCI,
wherein said motor imagery detection module determines said motor imagery of the person by using said stored selected corresponding features.

12. The system as claimed in claim 11, wherein the stimulation element comprises a tactile actuator.

13. The system as claimed in claim 11, further comprising a screen for providing visual feedback to the person based on the motor imagery, the movement, or both.

14. The system as claimed in claim 11, wherein the system is further operable to train the classifiers by performing non-linear regression using the selected corresponding features after the corresponding features have been selected by the trained classification algorithm and non-linear post-processing regression using an output from the non-linear regression.

* * * * *